(12) United States Patent
Christou et al.

(10) Patent No.: US 6,288,312 B1
(45) Date of Patent: Sep. 11, 2001

(54) METHOD OF CREATING TRANSFORMED RICE PLANT

(75) Inventors: Paul Christou, Madison; Tameria L. Ford, Waunakee; Matt Kofron, Madison, all of WI (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 08/143,511

(22) Filed: Oct. 26, 1993

Related U.S. Application Data

(63) Continuation of application No. 07/701,416, filed on May 15, 1991, now abandoned.

(51) Int. Cl.$^7$ .............................. C12N 15/82; A01H 4/00
(52) U.S. Cl. ...................... 800/320.2; 800/278; 800/288; 800/293; 800/300; 435/430; 435/430.1; 435/470
(58) Field of Search ............................. 435/172.3, 240.5, 435/470, 430, 430.1; 800/205, DIG. 57, 278, 288, 293, 300, 320.2; 935/53

(56) References Cited

U.S. PATENT DOCUMENTS

| | | | |
|---|---|---|---|
| 4,945,050 | 7/1990 | Sanford | 435/172.1 |
| 5,015,580 | * 5/1991 | Christou et al. | 435/172.3 |

FOREIGN PATENT DOCUMENTS

| | | | |
|---|---|---|---|
| 0301749 | 2/1989 | (EP) | C12N/15/00 |
| 63287485 | 11/1988 | (JP) | C12N/15/00 |

OTHER PUBLICATIONS

Sanford 1990 Physiologia Plantarum 79:206–209.*
Sanford 1988 Trends in Biotechnology 6:299–302.*
Wang et al 1988 Plant Molec Biol 11:433–439.*
De Block et al 1987 The EMBO J 6(9):2513–2518.*
Christou et al 1988 Plant Physiol. 87:671–674.*
Cao et al 1990 (Mar. 5) In Plant Gene Transfer, UCLA Symposium vol. 129, Lamb et al (eds,) Wiley–Liss pp. 21–33.*
Yamada et al 1984 In Handbook of Plant Cell Culture vol. 3, Evans et al (eds), Macmillan, pp. 151–169.*
Christou, et al., "Production of Transgenic Rice (Oryza sativa L.) Plants from Agronomically Important Indica and Japonica Varieties Via Electric Discharge Particle Acceleration of Exogenous DNA into Immature Zygotic Embryos," 9 Biotechnology 957–962, (Oct. 1991).
"Japanese DEvelop Disease–Resistant Rice Plant," 10 Biotechnology News 11 (1991).
Akagi, H. et al., "Construction of Rice Cybrid Plants," 215 Mol. Gen. Genet. 501–506 (1989).
Battraw and Hall, "Histochemical Analysis of CaMV35S Promoter–B–Glucuronidase Gene Expression in Transgenic Rice Plants," 15 Plant Molec. Biol. 527–538 (1990).

Datta, et al., "Genetically Engineered Fertile Indica–Rice Recovered from Protoplasts," 8 Bio/Technology 736–740 (1990).
Dekeyser, R.A., et al., "Transient Gene Expression in Intact and Organized Rice Tissues," 2 The Plant Cell 591–602 (1990).
Hartke and Lörz, "Somatic Embryogenesis and Plant Regeneration from Various Indica Rice (Oryza sativa L.) Genotypes," 43 J. Genet. & Breed. 205–214 (1989).
Hayashimoto, et al., "A Polyethylene Glycol–Mediated Protoplast Transformation System for Production of Fertile Transgenic Rice Plants," 93 Plant Physiol. 857–863 (1990).
Luo and Wu, "A Simple Method for the Transformation of Rice Via the Pollen–Tube Pathway," 6 Plant Molec. Biol. Rep. 165–174 (1988).
Luo and Wu, "A Simple Method for the Transformation of Rice Via the Pollen–Tube Pathway (Corrected Version)," 7 Plant Molec. Biol. Rep. 69–77 (1989).
Matsuki, R., et al., "Tissue–Specific Expression of the rol C Promoter of the Ri Plasmid in Transgenic Rice Plants," 220 Mol. Gen. Genet. 12–16 (1989).
Oard, et al., "Transient Gene Expression in Maize, Rice, and Wheat Cells Using an Airgun Apparatus," 92 Plant Physiol. 334–339 (1990).
Okada, K., et al., "Co–Electroporation of Rice Protoplasts with RNAs of Cucumber Mosaic and Tobacco Mosaic Viruses," 7 Plant Cell Reports 333–336 (1988).
Ozias–Akins, P. and I.K. Vasil, "Plant Regeneration from Cultured Immature Embryos and Inflorescences of Triticum aestivum L. (Wheat): Evidence for Somatic Embryogenesis," 110 Protoplasma 95–105 (1982).
Peng, et al. "Co–Transformation of Indica Rice Protoplasts with gusA and neo Genes," 9 Plant Cell Reports 168–172 (1990).
Potrykus, I., "Gene Transfer to Cereals: An Assessment," 8 Bio/Technology 535–542 (Jun., 1990).
Potrykus, I., et al., "Callus Formation from Cell Culture Protoplasts of Corn (Zea mays L.)" 54 Theor. Appl. Genet. 209–214 (1979).

(List continued on next page.)

Primary Examiner—David T. Fox

(57) ABSTRACT

A method of transforming rice is disclosed. The method begins with the preparation of copies of a nucleic acid construct that are coated onto biologically inert carrier particles. In one embodiment, the nucleic acid-coated carrier particles are physically accelerated toward immature rice embryos. In another embodiment, the nucleic acid-coated carrier particles are accelerated toward discs excised from the meristem region of a rice seedling. Both the bombarded embryos and discs are cultivated to produce shoots. These shoots are cultivated into whole sexually mature plants, some of which are transformed. The presence of the nucleic acid construct is verified in either the shoots or the sexually mature plants. A particularly advantageous embodiment of the invention is a transformed Indica rice plant.

7 Claims, 2 Drawing Sheets

OTHER PUBLICATIONS

Raineri, et al., "Agrobacterium–Mediated Transformation of Rice (*Oryza sativa L.*)," 8 *Bio/Technology* 33–38 (1990).

Shimamoto, et al., "Fertile Transgenic Rice Plants Regenerated from Transformed Protoplasts," 338 *Nature* 274–276 (1989).

Tada, et al., "Efficient Gene Introduction into Rice by Electroporation and Analysis of Transgenic Plants: Use of Electroporation Buffer Lacking Chloride Ions," 80 *Theor. Appl. Genet.* 475–480 (1990).

Terada and Shimamoto, "Expression of CaMV35S–GUS Gene in Transgenic Rice Plants," 220 *Mol. Gen. Genet.* 389–392 (1990).

Toriyama, K., et al., "Transgenic Rice Plants After Direct Gene Transfer into Protoplasts," 6 *Bio/Technology* 1072–1074 (1988).

Uchimiya, et al., "Expression of a Foreign Gene in Callus Derived from DNA–Treated Protoplasts of Rice (Orzya sativa L.)," 204*Mol. & Gen. Genet.* 204–207 (1986).

Yang, et al., "Production of Kanamycin Resistant Rice Tissues Following DNA Uptake into Protoplasts," 7 *Plant Cell Reports* 421–425 (1988).

Zhang, H.M., et al., "Transgenic Rice Plants Produced by Electroporation–Mediated Plasmid Uptake into Protoplasts," 7 *Plant Cell Reports* 379–384 (1988).

* cited by examiner

METHOD OF CREATING TRANSFORMED RICE PLANT

This application is a continuation of application Ser. No. 07/701,416, filed May 15, 1991, now abandoned.

BACKGROUND OF THE INVENTION

The present invention relates to the field of plant molecular biology. In particular, it relates to the creation of transformed rice plants via accelerated particles.

BACKGROUND

Rice, Oryza sativa, is an important food crop that provides more calories than any other cereal on a per hectare basis and is second only to wheat in area harvested worldwide. There is a great deal of interest in new rice varieties, but conventional plant breeding methods have several inherent limitations. Several generations of selfing are required for homozygosity, so breeding programs for new rice varieties may take several years. Genetic traits from wild rice varieties are potentially useful in improving rice resistance to pests, diseases, and adverse environment, but wild rice varieties do not cross well with domestic rice.

Because of the limits of conventional plant breeding, rice has been genetically engineered. Luo and Wu, *Plant Molec. Biol. Rep.* 6 [3]: 165–174 (1988) and *Plant Molec. Biol. Rep.* 7 [1]: 69–77 (1989), reported a method of transferring foreign DNA into recently pollinated rice florets which they term "pollen tube pathway" transformation. The pollen tube pathway process involves slicing away the top of the rice floret so that the stigma is cut off and the style has a severed end. A drop of a DNA-containing solution is placed at the cut end of the floret and allowed to flow down the pollen tube. Eventually, seeds are harvested and germinated. Pollen tube pathway transformation, however, has not been repeated by others and does not seem to be reproducible.

Rice protoplasts, the rice plant cell isolated from the cell wall, have been a popular target of genetic engineering. One common transformation method is to incubate the protoplasts with DNA and polyethylene glycol (PEG) and subsequently culture the protoplasts into plants in the presence of a selective agent. For example, Uchimiya et al., Mol Gen Genet: 204–207 (1986), describe PEG-mediated transformation of rice protoplasts to produce the expression of the foreign gene in transformed callus. Other examples of PEG-mediated protoplast transformation are found in Hayashimoto et al., *Plant Physiol.* 93: 857–863 (1990) and Peng et al., *Plant Cell Reports* 9: 168–172 (1990).

Rice protoplasts have also been transformed via electroporation. In most electroporation methods, rice protoplasts are mixed with a DNA solution and subjected to an electrical pulse. Similarly to PEG-mediated transformation, the DNA molecules cross the cell membrane and integrate into the cell genome. Recently, Terada and Shimamoto, *Mol. Gen. Genet.* 2201 389–392 (1990), have described the transformation of rice protoplasts via electroporation to produce mature rice plants that express the foreign gene. Tada et al., *Theor. Appl. Genet.* 80: 475–480 (1990), and Battraw and Hall, *Plant Molec. Biol.* 15: 527–538 (1990), have also recently reported transformation of rice via electroporation. Shimamoto, et al., *Nature* 338: 274–276 (1989), electroporated a hygromycin resistance gene into protoplasts and detected the foreign gene in progeny plants.

Rice has been transformed with a mixture of PEG and electroporation in Yang et al., *Plant Cell Reports* 7: 421–425 (1988). Transformation was confirmed by enzymatic assays in randomly chosen kanamycin resistant clones.

Transformation methods based on either PEG or electroporation also are limited because they depend on the regeneration of whole transformed rice plants from transformed rice protoplasts. There are many problems and limitations inherent in the protoplast culture regeneration process. Current protoplast regeneration processes result in a high frequency of somaclonal variation, albinism, and sterility. Additionally, and most importantly, not all rice varieties can be regenerated from protoplasts. Rice is grouped into two major groups of varieties, designated Japonica and Indica. Japonica and Indica varieties differ on the basis of their geographical distribution and morphological and physiological elements. Japonica and Indica varieties also differ in their amenability to tissue culture and regeneration methods. In general, Japonica varieties have high callus yield and high regeneration ability, and Indicas have very poor callus growth and poor regeneration potential. Indica varieties are, in general, the most commercially desirable.

The transformed rice plants produced by the procedures discussed above were Japonica varieties. Luo and Wu, *Plant Molec. Biol.* 7 [1]:69–77 (1989), included an Indica variety in their pollen tube pathway experiments. However, the reported positive transformation results have not been repeated and cannot be confirmed. Datta et al., *Biotechnology* 8: 736–740 (1990), have established a PEG-mediated transformation protocol for plant regeneration from Indica-type protoplasts. Southern analysis and enzyme assays have proved that the foreign gene was stably integrated and inherited in offspring. This method, however, only works on one specific, noncommercial Indica variety. This is the only reported method performed to date on Indica rice varieties that resulted in transformed plants. In general, while much effort has been expended on developing a reproducible system to regenerate Indica varieties, no such procedure has yet been published.

Rice has been transformed via Agrobacterium infection of mature embryos. The first widely used plant genetic engineering technique was based on the natural ability of the soil-dwelling microorganism *Agrobacterium tumefaciens* to introduce a portion of its DNA into a plant cell as a part of the normal pathogenic process. If a foreign gene is inserted into the bacteria in certain ways, the Agrobacterium can be used to transfer the foreign gene into a plant. Agrobacterium transformation techniques have been developed for a number of plants, mostly dicotyledonous, but the usefulness of the technique has varied from plant species to species. Agrobacterium-based transformation systems are limited, because they require cell or tissue culture and plant regeneration techniques. Plant lines vary in their amenability to tissue culture and regeneration methods. Monocots, such as rice, are especially poor candidates for Agrobacterium-mediated transformation. However, Raineri et al., *Biotechnology* 8: 33–38 (1990), report Agrobacterium-mediated transformation of rice tissues, as confirmed by DNA hybridization analysis. The inoculated embryos formed tumorigenic callus tissue. No plants were reported, and it appears that it may be impossible to regenerate plants from these tissues.

One new transformation technique attempts to create a transformed plants by bombarding plant cells or tissues with accelerated particles which carry genetic material. The first indication of the utility of this technique was a demonstration that DNA constructs could be coated onto tungsten particles and accelerated into onion skin, where the genes were transiently expressed. U.S. Pat. No. 4,945,050. A problem in the development of an accelerated particle transformation process is the difficulty of obtaining a germline plant transformation. By the term "germline transformation" it is meant that the germ cells of the plant are transformed in such a way that the progeny of the plant inherit the foreign nucleic acid construct inserted with the particles into the parental plant tissue. Plant genetic transformation has been achieved by the accelerated particle method. U.S. Pat. No. 5,015,580 discloses the germline transformation of soybean plants and plant lines. One method disclosed in that published patent application is accelerating DNA-coated particles into excised embryonic axes of soybean plants. If the bombarded soybean embryonic axes are treated with high cytokinin media, shoots are induced from the treated embryonic axes. When the shoots are cultivated into whole soybean plants, a significant percentage of the plants will have transformed germlines. Similar to particle bombardment, transformation of rice has been attempted with an air gun apparatus. Oard et al., *Plant Physiol.* 92: 334–339 (1990) report transient gene expression when embryogenic callus of rice is bombarded. For particle-mediated transformation efforts, however, it is far easier to obtain transient activity in callus than it is to obtain germline transformant plants.

The art of plant molecular biology needs an efficient method of creating a transformed Indica rice plant. This method would optimally not depend on protoplast culture and regeneration, should be genotype independent, and should readily create germline transformant plants which produce transgenic progeny. It would also be most desirable if the same procedure was available for Japonica varieties as well.

SUMMARY OF THE INVENTION

The present invention is both a method of creating transformed rice plants and transformed Indica rice plants. The method begins with the preparation of copies of a nucleic acid construct. These copies are coated onto biologically inert carrier particles. In one embodiment of the present invention, the nucleic acid-coated carrier particles are physically accelerated toward immature rice embryos. In another embodiment, discs are excised from the meristem of a rice seedling. These discs are bombarded with the nucleic acid-coated carrier particles. Both the bombarded embryos and discs are cultivated to produce shoots. These shoots are cultivated into whole, sexually mature plants. The presence of the nucleic acid construct is verified in either the shoots or the sexually mature plants.

One object of the present invention is to produce a transformed Indica rice plant.

Another object of the present invention is to produce an Indica rice plant with transformed progeny.

An advantage of the method of the present invention is that it is successful in all rice varieties.

Another advantage of the method of the present invention is that it does not depend on protoplast culture or embryogenic suspension culture, the regeneration protocols for which are much more genotype dependent.

Other objects, advantageous, and features of the present invention will become apparent from the following specification when taken in conjunction with the accompanying drawings.

DESCRIPTION OF THE PREFERRED EMBODIMENTS

Figure 1:
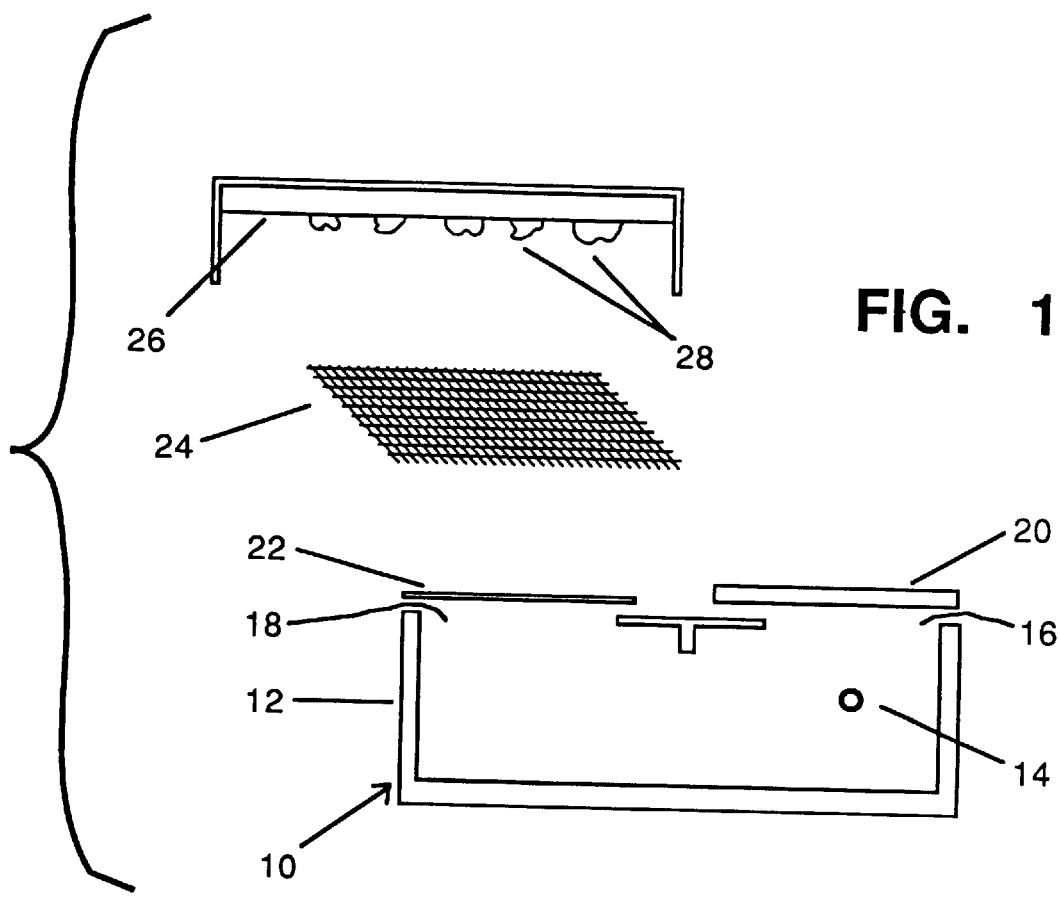
FIG. 1 is an exploded schematic view of a particle acceleration device useful in the present invention.

The present invention is a method of obtaining transformed rice plants. The general approach was to bombard meristem tissues to achieve a germline transformation. Meristem tissues are tissues in which the plant cells are dividing. Grasses and related monocots, such as rice, have meristematic tissues in the vicinity of the nodes, which are leaf attachment areas. The rice embryo also contains meristematic cells.

In processes for particle mediated genetic transformation, only a small percentage of the treated cells will be found to be transformed. Accordingly, a difficult part of the process is the identification of, or selection for, transformant cells or plants. This problem has led some investigators to work with single cell systems such as protoplasts, or suspension culture, on the theory that any regenerate plants would arise from single cells, thereby avoiding chimeric plants. However, the use of such single cell systems suffers from a severe disadvantage in that only certain rice genotypes can be regenerated from such cultures.

Another approach is to accelerate DNA-laden carrier particles into differentiated tissue, and that is the approach used here. This approach is not dependent on single cell cultures and is therefore genotype independent. A theoretical drawback of following this approach is that chimeric events might predominate, making it difficult to identify or find any germline transformant events. Surprisingly, it has been found that clonal, germline transformant shoots can be recovered at a practical frequency from bombarding meristematic rice tissue.

In one embodiment of the present invention, immature rice embryos are the target tissues. The embryos are bombarded with nucleic acid-coated particles, induced to form embryogenic or organogenic calli, and transformed plants are regenerated from the calli. From the plants produced through embryogenesis, clonal germline transformant plants are found at a reasonable frequency. In a second embodiment of the invention, discs are excised from the meristem region of a rice seedling. These meristem discs are cultured, and then bombarded with nucleic acid-coated particles. In both embodiments, the bombarded embryos or discs are cultivated to produce shoots. These shoots are regenerated into whole, sexually mature plants. The presence of the nucleic acid construct may be verified in either the shoots or the sexually mature plant.

A. Preparation of Rice Embryos and Meristem Discs

1. Preparation of Embryos

In the first embodiment of the invention, immature rice embryos must be isolated. Rice seed is isolated from the panicle of a mature rice plant and sterilized. The rice embryo, which is composed of the scutellum (the cotyledon) and the shoot/root axis, is excised from the seed coat by removing the endosperm. Preferably, immature embryos are excised. By "immature" we mean that the embryos are approximately 0.5 mm to 1.5 mm in length and approximately 10–18 days from anthesis. Mature embryos may be used in the present invention, but it is more difficult to culture these embryos. Very immature embryos may be used, but the size of the embryos may be difficult to manipulate, the embryos may more easily be damaged by blasting, and such smaller embryos have also exhibited poor transformation efficiencies in transient expression experiments.

After excision, the rice embryos are preconditioned for transformation. By "preconditioning" it is meant that the excised tissue is placed on a medium amenable to embryo culturing immediately prior to transformation. For reasons that are still obscure, the preconditioning procedure seems to increase the efficiency of the transformation process, resulting in greater number of transformants than could be obtained without it. For Indica varieties a suitable culture medium is CC medium as defined by Potrykus, et al., *Theor. Appl. Genet.* 54: 209–214 (1979), and summarized in Table 1. This medium contains salts, sugars and an auxin, 2,4-D. We typically supplement CC medium with additional 2,4-D and casein hydrolysate. For Japonica varieties a suitable medium is MS medium containing 0.5 mg/l 2,4-D. MS medium is defined by Murashige and Skoog, *Physiol. Plant* 15: 473–497, 1962.

Typically, the excised embryos remain on the preconditioning medium for 24–48 hours at 25° C. in the dark. The embryo axis should touch the media, and the scutellum should be exposed. After preconditioning, the embryos are bombarded with nucleic acid-coated particles, as described below. While this preconditioning is preferred, it may not be an absolute requirement for successful transformation that the preconditioning be on any particular medium.

In general, it seems as if there is an advantage to excision of this tissue explant 24–48 hours prior to particle blasting. Although the particular medium does not seem critical, excised and aged (24–48 hours) embryos result in a significant increase in transient expression activity of the inserted genes over comparable embryos which are freshly blasted.

TABLE 1

| CC media | |
|---|---|
| $KNO_3$ | 1212.0 mg/l |
| $NH_4NO_3$ | 640.0 mg/l |
| $CaCl_2.2H_2O$ | 588.0 mg/l |
| $MgSO_4.7H_2O$ | 247.0 mg/l |
| $KH_2PO_4$ | 136.0 mg/l |
| $FeSO_4.7H_2O$ | 27.8 mg/l |
| $Na_2EDTA$ | 37.3 mg/l |
| $H_3BO_3$ | 3.1 mg/l |
| $MnSO_4.4H_2O$ | 11.15 mg/l |
| $ZnSO_4.7H_2O$ | 5.76 mg/l |
| KI | 0.83 mg/l |
| $Na_2MoO_4.2H_2O$ | 0.24 mg/l |
| $CuSO_4.5H_2O$ | 0.025 mg/l |
| $CoSO_4.7H_2O$ | 0.028 mg/l |
| nicotinic acid | 6.0 mg/l |
| thiamine-HCl | 8.5 mg/l |
| pyridoxine-HCl | 1.0 mg/l |
| glycine | 2.0 mg/l |
| m-inositol | 90.0 mg/l |
| coconut water* | 100.0 ml/l |
| sucrose | 20.0 g/l |
| mannitol | 36.43 g/l |
| pH(KOH) | 5.8 g/l |
| 2,4-D | 2.0 mg/l |
| filter sterilized | |

*Gibco no. 570–5180, undiluted

2. Preparation of Meristem Discs

Another embodiment of the invention involves the transformation of rice plants beginning with meristem disc tissues. There are no differences in our methods of preparing and regenerating meristem discs from either Japonica or Indica variety rice, although Indica varieties appear slightly more responsive. To obtain meristem discs, mature dry rice seed is sanded to remove the pericarp and sterilized. The seeds are then treated to induce germination. The seeds are plated on medium and under light and temperature conditions that provide elements needed for growth of the seedling. Typically, this is a sixteen hour photoperiod at 26° C. A suitable medium for growth is ½ MS medium with supplemented sucrose, Carbencillin, Cefotaxime, and Benlate. Small seedlings of approximately three inches are formed after 5–7 days.

A meristem disc is excised from these seedlings by making small horizontal cuts at the junction of the rhizosphere and the shoot apex. An approximately 0.5 to 1.5 mm thick disc can be excised from this junction. The discs are preconditioned on a medium amendable to cell culture, such as CC medium with supplemented 2,4-D, and casein hydrolysate. Typically, the discs are preconditioned for 24 hours at 25° C. in the dark under conditions of low oxygen achieved by bubbling pure nitrogen through the containers in which the tissues were placed. After preconditioning, the discs are bombarded with nucleic acid-coated particles.

B. Preparation of Nucleic Acid-Coated Particles

Multiple copies of the nucleic acid construct, either RNA or DNA, are prepared by known molecular biology techniques. By "nucleic acid constructs" it is meant to describe any RNA or DNA molecule capable of functioning within a rice cell. A suitable nucleic acid construct might be an isolated or constructed gene with accompanying regulatory signals, or might be a population of RNA or DNA molecules. The nucleic acid might originate in rice, or in any other species.

To be useful in a particle-mediated transformation process, the nucleic acid construct must be capable of performing some useful function in the cells of target plant tissues. The transforming genetic construct will normally be a chimeric construct in the sense that its genetic material originates from more than one kind of organism. The genetic construct could be one that is capable of expressing a gene product in the target tissues. Such gene products will typically be a foreign protein, but could be other gene products as well, as such as an antisense RNA construct intended to inhibit an endogenous plant system.

Foreign genetic constructs are often embodied in expression cassette vectors for plant cells, many of which are known in the art. Typically such a plant expression vector system includes the coding sequence for the desired foreign gene and appropriate regulatory sequences. The appropriate regulatory sequences might include a promoter sequence capable of initiating transcription and a translational terminator. Some promoters and transcription terminators found to be effective in other plants are effective in rice as well. A translation or transcriptional enhancer may be incorporated between the promoter and the coding region of the genetic sequence.

The transforming nucleic acid construct may include a marker gene which can provide selection or screening capability in the treated plant tissues. Selectable markers are generally preferred for plant transformation events, but are not available for all plant species. A selectable marker conditions for a trait in the transformed plant cells which can be selected for by the exposure of the plant tissues to a selective agent. Suitable selectable markers can be antibiotic or herbicide resistant genes which, when inserted in some cells of a plant in culture, would imbue those particular cells with the ability to withstand exposure to the antibiotic or the herbicide.

Another type of marker gene is one that can be screened by histochemical or biochemical assay, even though the gene cannot be selected for. A suitable marker gene found useful in such plant transformation experience is the GUS gene. Jefferson et al., *EMBO J.*, 6: 3901–3907 (1987), disclose the general protocol for a GUS assay. The GUS gene encodes an enzyme that catalyzes the cleavage of 5-bromo-4-chloro-3-indolyl glucuronide, a substrate that has a blue color upon cleavage. Thus, the use of a GUS gene provides a convenient assay for the detection of the expression of introduced DNA in plant tissues by histochemical analysis of the plant tissues. In a typical transformation process, the gene sought to be expressed in the plant could be coupled in tandem with the GUS gene. The tandem construct could be transformed into plant tissues, and the resulting plant tissues could be analyzed for expression of the GUS enzyme.

Figure 3:
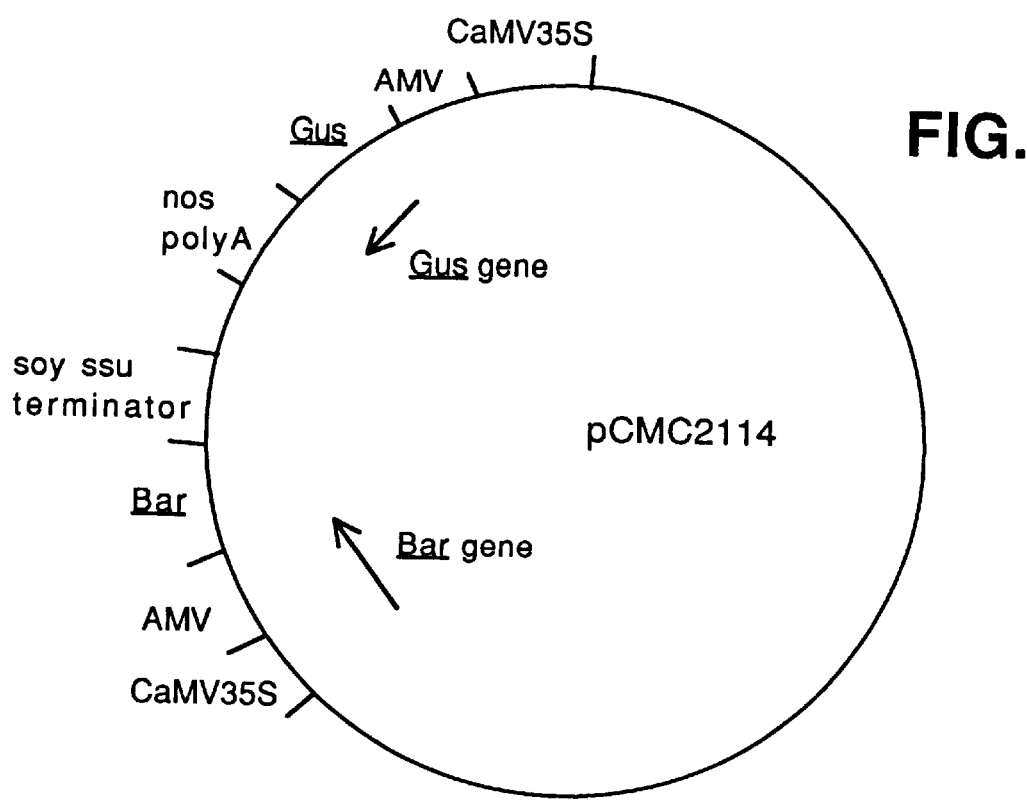
FIG. 3 is an illustration of the plasmid pCMC2114 used in the Example.

In our Examples, we have used plasmid pCMC2114, described in FIG. 3. This plasmid contains the gene encoding GUS and the Bar gene. The Bar gene encodes resistance to certain herbicides, such as Bialaphos, and provides a selection agent since transformed plants can grow in the presence of the herbicide.

The transformation process requires carrier particles of a durable, dense, biologically-inert material. Gold is a suitable material for use as the carrier particle. The carrier particles are of extremely small size, typically in a range of one to three microns, so that they are small in relation to the size of the rice target cells. The inventors here and their coworkers have used two physical forms of gold carrier particles. One form consists of small spherical gold particles sold at a nominal size range (in microns) and typically varying ±50% in size with each batch. The other form consists of microcrystalline gold or gold powder in which the metal appears, upon microscopic examination, to be flakes or flattened crystals of irregular shape and which vary quite widely in size. Preferably, the microcrystalline gold particles are used as carrier particles. A preferred source of microcrystalline gold particles is "Gold powder A1570" from Engelhart Corporation of East Brunswick, N.J. It has been found that microcrystalline carrier particles of irregular size achieve a higher transformation efficiency than that achieved by spherical gold particles.

The genetic material to be inserted into the cells is coated onto the carrier particles. This can be readily done by precipitating solutions of DNA or RNA onto the carrier particles themselves. Suitable stabilizers can be added to the mixture to help with the longevity of the genetic material on the carrier particles.

A typical method of coating nucleic acid constructs onto gold beads is as follows: 10 mg of amorphous crystalline gold is measured into the bottom of a 1.5 ml Eppendorf microfuge tube. Care should be taken to ensure that the gold does not spill on the sides of the tube, since that would make it difficult to resuspend the gold in the small volumes used in the preparation process. 100 μl of a buffer is added, and the tube is vortexed gently, the buffer being 150 mM NaCl, 10 mM Tris-HCl, pH 8.0. 20.0 micrograms of plasmid DNA are added to the microfuge tube, and the tube is vortexed gently for 5–10 seconds. 100 μl of 0.1 M spermidine solution (free base) is added to this microfuge tube, and the microfuge tube is vortexed. 100 μl of 25% PEG solution (MW 1300–1600) is added, and the tube is vortexed well. While the DNA/carrier particle/PEG mixture is vortexed, 100 μl of 2.5 M $CaCl_2$ should be added drop-by-drop to the tube. The vortex is stopped, and the tube is incubated at room temperature for 10 minutes. At this point, the nucleic acid has precipited out of solution and onto the gold.

The mixture of DNA and carrier particles is given a brief spin in a microfuge. The cleared supernatant is completely removed. The precipitate, consisting of the DNA and carrier particles, is resuspended in 10 mls of 100% ethanol. The resuspended DNA and carrier particle mixture is sonicated two to three times for one second in a water bath sonicator. This preparation can be stored for some time. The resulting suspension is then coated onto an 18×18 mm carrier sheet at a rate of 163 μl per carrier sheet, or a calculated rate of 0.05 milligrams per square centimeter of the carrier sheet. In summary, the gold particles are coated with DNA at a level of approximately 2 μg DNA/1 mg particles, and the particles are resuspended at a concentration of 0.5–1.0 mg particles/1 ml ethanol.

C. Bombarding Cultured Embryos and Meristem Discs

The apparatus utilized in the present invention must be capable of delivering the nucleic acid-coated particles into plant cells in such a fashion that a suitable number of cells can be transformed. At some frequency, the carrier particles lodge within the rice cells and, through a poorly understood process, the genetic material leaves the carrier particles and integrates into the DNA of the host rice cells. Many types of mechanical systems can accelerate the carrier particles into plant cells. Possible mechanisms include ballistic explosive acceleration of particles, centrifugal acceleration of particles, electrostatic acceleration of particles, or other analogous systems capable of providing momentum and velocity to small particles.

The mechanism we used in the Example is based on the acceleration of particles through an adjustable electric voltage spark discharge device which is capable of accelerating a planar carrier sheet at a target surface. This apparatus will be described further below with reference to FIGS. 1 and 2.

The particle acceleration apparatus is generally indicated at 10 of FIG. 1. The apparatus consists of the spark discharge chamber 12 into which are inserted two electrodes 14 spaced apart by a distance of approximately one to two millimeters. The spark discharge chamber 12 is a horizontally extended rectangle having two openings, 16 and 18, extending out its upward end. The opening 16 is covered by an access plate 20. The opening 18, located on the side of the rectangle of the spark discharge chamber opposite from the electrode 14, is ultimately intended to be covered by a carrier sheet 22.

The electrodes 14 are connected to a suitable adjustable source of electric discharge voltage (not shown). A suitable source of electric discharge voltage includes a capacitor in the size range of one to two microfarad. The voltage of the charge introduced into the capacitor should be adjustable. An adjustable voltage can be introduced readily into such a capacitor through the use of an autotransformer which can be adjustable between a range of one and fifty thousand volts. Preferably, a high voltage electric switch is provided so that the capacitor can be discharged safely through the electrodes 14 without harm to the operator.

A carrier sheet 22 is placed upon the opening 18 of the spark discharge chamber 12. The carrier sheet 22 is a planar sheet of relatively stiff material which is capable of carrying small, inert carrier particles thereon toward the target surface. Preferably, the carrier sheet 22 is a small sheet of aluminized, Saran-coated mylar. We envision that other relatively stiff, planar materials may be used for the carrier sheet 22. The function of the carrier sheet 22 is to convert an outwardly outstanding force produced by the electrodes to a broadly distributed horizontal force capable of accelerating a large number of carrier particles in parallel with an even force. Other kinds of force other than electric discharge can be used to propel the carrier sheet 22 upward. The force should be adjustable so that the force of travel of the carrier sheet 22 can be adjusted.

Figure 2:
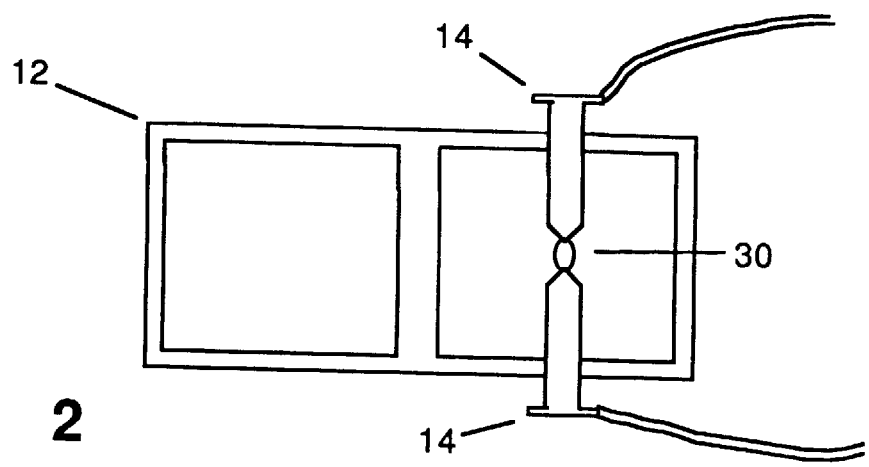
FIG. 2 is a top plan view of the device of FIG. 1.

Again referring to the apparatus of FIGS. 1 and 2, a retaining screen 24 is approximately 15 millimeters above the opening 18 and the discharge chamber 12. A target surface 26 is placed above the retaining screen 24 at a distance of between 5 and 25 millimeters. The target surface 26 is any suitable culture surface onto which the rice tissue to be transformed can readily be placed. We found that an overturned petri dish can be used for the transformation of plant tissues. Using a solid agar-based medium in the bottom of a petri dish, it is possible to place rice tissues on the agar where they will be retained. The petri dish itself can serve as the target surface while retaining the rice tissues on the agar.

The DNA-coated particles are layered onto the top of the carrier sheet 22. The layering is done so as to distribute a relatively even pattern of carrier particles across the entire top surface of the carrier sheet 22. Preferably, the coated carrier particles are applied to the carrier sheet at a loading rate of 0.025 to 0.050 milligrams of coated carrier particles per square centimeter of carrier sheet. The carrier sheet 22 is placed upon opening 18. The target surface 26 with the rice tissue on it is placed in position above the retaining screen 24. A small droplet of water, preferably 10 microliters, is placed in the chamber bridging between the ends of the two electrodes 14. The access cover 20 is placed in position on top of the spark discharge chamber 12.

At this point, the entire apparatus is enclosed in a vacuum chamber and a vacuum is drawn down into the range of approximately 500 millimeters of mercury. As the vacuum is drawn, a supply of helium is bled into the vacuum chamber. Thus, the vacuum chamber contains a relative vacuum compared to the atmosphere and the atmosphere within the vacuum contains helium. The lower density of helium, combined with the reduced pressure, lowers the drag on both the carrier sheet 22 and the carrier particles. At the same time, since the access plate 20 and the carrier sheet 22 were placed on the discharge chamber 12 prior to the vacuum being drawn, within the discharge chamber 12 there remains a higher pressure of pure air which is not yet displaced by helium.

The accelerated particle transformation process is initiated at this point. The voltage from the capacitor is electrically discharged to the electrodes 14. The voltages used in the present process have been in the range of 10–25 kV. The range of 10–16 kV is preferred. The voltage is discharged through the use of appropriate electric switching described above. The force of the electric discharge initiates a spark which leaps the gap between the electrodes 14 and vaporizes the small droplet of water which was placed between the electrodes. The vaporization force creates a violent atmospheric shock wave within spark discharge chamber 12. The shock wave radiates outward from the electrodes in all directions. Because of the immovable sides of the chamber, the impact of the radiating shock wave upon the interior of the discharge chamber 12 is focused towards the carrier sheet 22, which is then propelled upward with great velocity. The upwardly traveling carrier sheet 22 accelerates upward at great force until it contacts the retaining screen 24. The displacement of the remaining atmosphere in the chamber with helium assists in the travel of the carrier sheet 22, since helium provides less drag on the flight of the carrier sheet as well as on the carrier particles themselves. At the retaining screen 24, the carrier sheet 22 impacts the retaining screen 24 and is retained. The nucleic acid-coated particles, in contrast, fly off of the carrier sheet and travel freely toward the target rice tissues. The small carrier particles then hit the rice tissue on the target surface and proceed into the tissue cells.

D. Regeneration of Rice Plants

Plants must be created from the bombarded embryo and meristem disc tissues. At either the cellular or plant level, the plants must be screened or selected to segregate the transformed tissues and plants from the nontransformed tissues and plants because in most particle-mediated plant transformation events, the nontransformed plants will be the majority of the recovered plants. For example, rice embryos and meristem discs bombarded with pCMC2114 can be grown in the presence of the herbicide Bialaphos, to select transformed plants from nontransformed plants. To perform the selection, either continuous exposure to the selective agent or a pulse of the agent may be used. To determine whether the plant has a transformed germline, the plant's progeny must be assayed for presence of the inserted foreign gene or genes. The selection protocol has not proven totally effective, due to significant number of non-transformant escapes. The use of selection is still useful, however, since it enriches the pool of potentially transformant plants which must be screened in the sense that a higher percentage of selected plants will be transformed compared to the percentage recovered from unselected plants.

1. Regeneration from Indica Embryos

First, callus must be induced from the transformed cells. Callus induction methods are well-known in the art of plant biology. For example, Hartke and Lorz, *J. Genet. & Breeding* 43: 205–214 (1989), have described somatic embryogenesis and plant regeneration from various Indica genotypes. An MS medium with 2,4-D added may also be used, but seems to give less optimum results. Bombarded embryos are transferred to a medium that promotes callus growth. A suitable medium is CC medium supplemented with 1 g/l casein hydrolysate and 2 mg/l 2,4-D. A suitable growth condition is 25° C. in the dark. After approximately four weeks, callus forms.

Shoots must be induced from the transformed callus. A suitable shoot induction medium is CC medium containing 0.05 mg/l zeatin and 1 mg/l IAA. (This combination is termed "CCIZ1".) Suitable growth conditions are 16 hour photoperiod at 26° C. Shoots typically appear after 10–20 days. Shoots are then separated for subculture on CCIZ1. These shoots, or any other bombarded or transformed tissue, may be assayed for the presence of the foreign gene. Shoots are rooted on a suitable medium, such as ½ MS medium with 20 g/l sucrose and 0.5 mg/l IBA, and develop into mature rice plants. Mature plants may be assayed for the presence of the foreign gene.

2. Regeneration from Japonica Embryos by Embryogenesis

The regeneration of Japonica embryos is very similar to that of Indica embryos. However, MS medium is generally preferred over CC medium for Japonica. After bombardment, the Japonica embryo is placed on MS medium containing 0.5 mg/l 2,4-D to induce callus growth. After approximately two weeks, calli are transferred to a shoot-promoting medium such as MS medium containing 50 g/l sucrose, 2 mg/l kinetin, 1 mg/l NAA, 0.8% washed agar and 300 mg/l casein hydrolysate. (This combination is termed "MS+" .) Suitable growth conditions are 16 hour photoperiod at 26° C. Shoots develop after 7–14 days and are removed to a medium promoting further growth, such as MS medium containing 1 mg/l IAA and 1 mg/l zeatin. Individual shoots are placed on a root-conditioning medium, such as ½ MS medium with 20 g/l sucrose and 0.5 mg/l IBA and develop into mature plants. As with Indicas, either transformed tissue or mature plants can be assayed for the foreign gene.

Regardless of the variety, Japonica, Indica or mixed, the regeneration of plants can be done most easily by embryogenesis, but may also involve organogenic shoots. Embryogenesis refers to the process by which a somatic embryo develops through a developmental pattern similar to zygotic embryogenesis into a whole plant. Embryogenic shoots predominate in the regeneration protocols described above. The embryogenic shoots seem as if they originate from single cell primordia since they are clonal, or non-chimeric. Organogenic processes involve the development of organic structure (i.e. shoots or roots) from differentiated tissue structures and will usually give rise to chimeric plants. Surprisingly, in these callus cultures, embryogenic regeneration predominates and clonal transformant embryos are recovered at relatively high frequencies.

3. Regeneration from Meristem Discs using Organogenesis

After meristem discs have been bombarded, the discs should be immediately transferred to a medium that promotes shooting. A suitable medium is MSR medium (MS medium with BAP at 0.38 mg/l and IBA at 0.4 mg/l with a 16 hour photoperiod at 26° C. After these discs begin to form shoots, the disc should be transferred to MS+ medium (described supra). Typically, multiple shoots and roots will form. These shoots should be transferred to a root-promoting medium such as ½ MS medium with 0.5 mg/l IBA for further rooting to develop mature plants. As with regenerated embryos, either the shoots or the mature plants can be assayed for the presence of the foreign gene.

EXAMPLE

A. Transformation of Rice Embryos using Japonica Procedure

Seeds were harvested from greenhouse-grown Gulfmont rice, a variety popular in the U.S. As this experiment was performed, it was believed that Gulfmont was a pure Japonica variety. Later detailed pedigree information indicated that this is not the case and Gulfmont may include both Indica and Japonica heritage. The immature seeds were sterilized by soaking in bleach for five minutes and then rinsed extensively in a solution of SDW (sterile distilled water) and CCB (carbencillin at 400 mg/l, cefotaxime at 100 mg/l, and benomyl at 50 mg/l). The bracts surrounding the seeds were removed microscopically and the seeds were again placed in a mixture of SDW and CCB. The immature seeds were sterilized again in 50% bleach for one minute and rinsed four times in a mixture of SDW and CCB.

The immature embryos were excised from the sterilized seeds. These embryos were between 0.5 and 1.5 mm in size. The excised embryos were plated with the scutellum up on CC medium additionally containing 2.0 mg/l 2,4-D and 1 g/l casein hydrolysate and kept in the dark at 25° C. for 24 hours.

After 24 hours of preconditioning, the embryos were bombarded with carrier particles coated with plasmid pCMC2114 (FIG. 3). In this Example, approximately 100 embryos were bombarded at 10–16 kV. For two days after bombardment, the explants were plated on MS medium to which had been added 2,4-D at 0.5 mg/l and Bialaphos at 10 mg/1. Bialaphos selection was maintained throughout the culture on MS+ media. Subsequently, the embryos remained two weeks on callus induction medium.

After callus has been induced, the calli are transferred to MS+ medium and moved to sixteen hour photoperiod at 26° C. Shoots developed from this callus. As the shoots developed they were removed for further culture on MS medium additionally containing 1 mg/l IAA and 1 mg/l zeatin. The individual shoots were rooted on ½ MS medium containing 20 g/l sucrose and 0.5 mg/l IBA.

Out of 100 explants, eighteen shoots were recovered. When subjected to a GUS histochemical assay, three shoots were at least partially positive. One shoot was destructively assayed and was entirely blue. Another shoot showed a positive reaction in a polymerase chain reaction, PCR, assay but appeared to be a nongermline transformant. Another shoot that had given a positive PCR assay for a small section of the shoot was taken to the greenhouse and planted in a rice mix (equal parts sand, peat, perlite, and soil). This plant has now matured and has progeny. The plant itself (RO) was found to express both the GUS and BAR genes in all the leaves of the plant. A Southern blot analysis of the DNA of the plant verified the presence of the DNA for both genes. Such results indicate that this rice plant has a transformed germline. Progeny of the plant have been found to express the products of genes encoded by pCMC 2114. Segregation of the transgenes in the first progeny (R1) generation has been at the expected ratio of 3:1.

Several hundred R1 progeny of the plant have now been raised to maturity. Southern blot analysis has confirmed stable integration and inheritance of the inserted DNA. The plants are also very resistant to glutamine synthase inhibitor herbicide application. Application of herbicide BASTA (a trade name for Bialaphos) at a rate of 500 ppm in foliar application has not visibly injured the plants, which continue to grow and maintain vigor. In destructive assays (for GUS), transformed clonal embryos could be recovered at a rate of between 10% and 50% of the recovered embryos, with or without selection.

B. Transformation of Indica Rice Embryos

The method of transforming Indica rice practiced here is very similar to that of Japonica rice. The bombarded Indica embryos have been cultured on a medium that is more optimal for their growth.

Seeds were harvested from the panicles of greenhouse-grown IR54 rice, an Indica variety. The immature seeds were sterilized by soaking in 50% bleach for 5 minutes and rinsed extensively in a mixture of SDW and CCB. The bracts surrounding the seed were removed microscopically, and the seed was placed in a mixture of SDW and CCB. The immature seed is again sterilized in 50% bleach for one minute and rinsed four times in SDW and CCB.

Immature embryos of 0.5 mm to 1.5 mm were excised from the seed coat and preconditioned for transformation on CC medium (Table 1) supplemented with 1 g/l Casein hydrolysate and 2 mg/l 2,4-D. The embryos were placed in the dark at 25° C. After 24 hours on this medium, the embryos were bombarded with nucleic acid-coated carrier particles, as described above. In this example, approximately 100 embryos were bombarded at 10 kV with particles coated with plasmid pCMC1515. The plasmid pCMC1515 is similar to pCMC2114, except that instead of a coding sequence for the BAR gene, it includes a coding sequence for hygromycin resistance.

After bombardment, the embryos were placed on CC medium with 1 g/l casein hydrolysate and 2 mg/l 2,4-D remained in the dark at 25° C. for four weeks. Two days after blasting, hygromycin selection was imposed for two weeks. After four weeks the calli were transferred to CC medium containing 0.05 mg/liter zeatin and one mg/l IAA under a 16 hour photoperiod at 26° C. Shoots appeared and were separated for subculture on CCIZ1. Separate shoots were rooted on ½ MS medium with 20 g/l sucrose and 0.5 mg/l IBA.

We have assayed large numbers of shoots for GUS activity via the standard histochemical assay. Nongermline transformant plants have been recovered regularly. A germline transformant plant has also been identified, which is PCR positive for both of the transgenes, and which expresses GUS well in all its tissues..

C. Transformation of Meristem Discs, and Regeneration by Organogenesis

Transformation via meristem discs is independent of rice genotype. Although the rice plant from which the discs in the example below were taken was an Indica rice, Japonica rice can be transformed in an almost identical manner. Dry seeds were removed from greenhouse-grown rice plants and sanded to remove the pericarp. The sanded seeds were sterilized by rinsing one time in 95% ethanol. The seeds were then rinsed in SDW with Carbencillin (400 mg/l), Cefotaxime (100 mg/l), and Benlate (0.05 g/l).

The sterilized seeds were then imbibed in a mixture of SDW and CCB (described supra) plus 1% "Antilife". Antilife is: Bravo (WP 75%) 10.0 g/l, Benomyl (DF 50%) 10.0 g/l, and Captan (WP 50%) 10.0 g/l. The seeds are imbibed at 28° C. in the dark for 24 hours. After imbibition, the seeds were soaked in 50% bleach for ten minutes. The sterilized seeds were rinsed five times in a mixture of SDW and CCB.

The sterilized seeds were plated embryo side up on ½ MS medium with 20 mg/l sucrose, 400 mg/l Carbencillin, 100 mg/l Cefotaxime, and 0.05 g/l Benlate at 26° C. under a 16 hour photoperiod. During this time, small rice seedlings appeared. After approximately 5–7 days, discs were excised from the seedling region at the junction of the rhizosphere and the shoot apex. This is the meristem region of the seedling. These discs were excised by making two horizontal cuts at this junction. A 0.5 to 1.5 mm thick disc was obtained.

The meristem discs are preconditioned for twenty-four hours in the dark on CC medium supplemented with 2 mg/l 2,4-D and under conditions of low oxygen. After twenty-four hours of preconditioning, the meristem discs were ready to be bombarded. In this example, 50 meristem discs were bombarded at 12–18 kV with particles coated with plasmid pCMC2114 (FIG. 3). The bombardment conditions were as disclosed above.

After bombardment the discs were transferred immediately to MSR medium. The bombarded discs were plated basal end down onto MSR medium under a sixteen hour photoperiod at 26° C. After approximately 2 weeks the discs began to form shoots. When the shoots reached 5 to 10 mm, after approximately 3–5 days, the entire disc/shoot complex was transferred to MS+ medium for one to two weeks. At this time, multiple shoots and roots formed. The entire complex was then transferred to culture in 50% strength MS medium to which had been added 20 g/l sucrose and 0.5 mg/l IBA, and cultured for one week prior to splitting. The complex was split up into individual shoots and transferred to ½ MS medium with 0.5 mg/l IBA for further rooting.

As of the present time no germline transformed plants have been obtained by this method. However, germline transformants are to be expected based on the number of chimeric plants that we have seen to date. Of the original 50 discs bombarded, 9 shoots were found to be positive when assayed by PCR. Shoots that gave a positive PCR were transferred to the greenhouse for further growth. In other species and systems, recovery of chimeric plants at this efficiency has also led to the recovery, at a lower efficiency, of germline transformant events.

D. Selection of Transformants

In the embryo recovery systems for Japonica and Indica described above, selection and/or enrichment of putative transformants by herbicide or antibiotic stress appears functional. Several callus cultures were transferred to embryonic induction medium to which had been added Bialaphos at 10 mg/l. In repeated experiments terminated by a terminal assay (for GUS), the calli yielded large numbers of shoots, of which many assayed as clonally transformed. Thus, although the selection may not be complete, the enrichment of the recovered shoot population seems to justify such selection.

We claim:

1. A method of creating germ-line transformed rice plants and seed comprising the steps of:

(a) preparing copies of a nucleic acid construct;

(b) coating the nucleic acid construct copies onto biologically inert carrier particles, the nucleic acid construct including a selectable marker conferring resistance to a selection agent;

(c) isolating an immature rice embryo;

(d) placing the isolated embryo on a target surface, wherein the embryo is intact;

(e) bombarding the embryo with the nucleic acid-coated carrier particles wherein the particles are physically accelerated toward the target surface in such a fashion that some particles lodge in the interior of at least some of the embryo cells;

(f) cultivating the bombarded embryo such that embryogenic callus is induced and shoots arise from the callus, such cultivating of the callus being done in the presence of a selection agent which is toxic to tissues not transformed with the selectable marker so as to enrich the percentage of shoots which contain the nucleic acid construct;

(g) cultivating the shoots formed in step (f) into whole sexually mature plants and obtaining progeny seed from such plants; and (h) verifying the presence of the nucleic acid construct in progeny plants from the seed of the mature plants of step (g).

2. The method of claim 1 wherein the embryos are preconditioned before step (e).

3. The method of claim 2 where the preconditioning includes culturing the embryos in the presence of an auxin.

4. The method of claim 1 wherein the length of the excised embryo is approximately 0.5 to 1.5 mm.

5. The method of claim 1 wherein the excised embryo is of an Indica variety.

6. The method of claim 1 wherein the excised embryo is of a Japonica variety.

7. The method of claim 1 wherein the selection agent is the herbicide Bialophos.

* * * * *